United States Patent [19]

Dunikowski et al.

[11] 4,048,844
[45] Sept. 20, 1977

[54] ELECTRIC SYSTEM OF METER FOR MEASUREMENTS OF DENSITY OF MIXTURES CONVEYED IN A PIPELINE

[76] Inventors: Andrzej Dunikowski, ul. Sienkiewicza 26; Jan Bednarczyk, ul. Chodowieckiego 5 m.39, both of Krakow; Jerzy Keska, powiat Krakow, Jaskowice 1; Tadeusz Pisarkiewicz, powiat Mlawa, Rydzyn Szlachecki; Andrzej Zamarski; ul. Marchlewskiego 22/2, Krakow, all of Poland

[21] Appl. No.: 669,461

[22] Filed: Mar. 22, 1976

Related U.S. Application Data

[63] Continuation of Ser. No. 503,911, Sept. 6, 1974, abandoned.

[51] Int. Cl.$^2$ .................. G01N 27/22; G01N 9/00
[52] U.S. Cl. .................. 73/32 R; 73/61.1 R; 324/61 QS
[58] Field of Search .................. 324/61 R, 61 QS; 73/32 R, 61.1 R

[56] References Cited

U.S. PATENT DOCUMENTS

| | | | |
|---|---|---|---|
| 2,985,826 | 5/1961 | Fluegel | 324/61 R |
| 3,176,222 | 3/1965 | Atkisson | 324/61 R |
| 3,635,082 | 1/1972 | Prellwitz et al. | 324/61 R X |
| 3,839,911 | 10/1974 | Zimmerman et al. | 73/231 M X |

Primary Examiner—James J. Gill

[57] ABSTRACT

Electric system for a meter for measurements of density of the mixtures conveyed in pipelines. The system has a capacity sensor installed in a pipeline and being connected, via a capacitance transducer, with a system compensating temperature induced variations in capacity. The input of the said system is connected with a temperature sensor installed in the pipeline, while the output of the said system is connected with an indicator-recording system. Instead of being connected with the input of the system, the temperature sensor can be connected with the capacitance transducer which is then connected directly with the indicator-recording system. In the case of the mixture temperature's being constant or varying within a narrow range, the electric system of the meter comprises a capacity sensor connected, via the capacitance transducer directly with the indicator-recording system.

2 Claims, 2 Drawing Figures

ELECTRIC SYSTEM OF METER FOR MEASUREMENTS OF DENSITY OF MIXTURES CONVEYED IN A PIPELINE

CROSS-RELATED APPLICATION

This application is a continuation of co-pending application Ser. No. 503,911 filed Sept. 6, 1974 and now abandoned.

FIELD OF THE INVENTION

The invention relates to an electric system for a meter for measurements of density of mixtures conveyed in pipelines, said system operating on the basis of the electric performance of the mixtures, said performance being influenced by variations in the component content. Which are conveyed in pipelines, and particularly mixtures of liquids and solids, require constant checking of their density.

BACKGROUND

Mixtures

Until recent times, instruments operating on mechanical and radioisotope principles have been in use for measurements of density of mixtures conveyed in pipelines. To the instruments operating on mechanical principle belongs, for instance, a meter metering the weight of mixture conveyed versus the known volume of this mixture, together with a system indicating the weight of the instrument itself. The operating principle of a meter of this type is based on measurement of the weight of a certain section of pipeline together with the weight of mixture conveyed through the said section of the pipeline. The weight of such a pipeline section depends on the density of the mixture which is being conveyed through the said section. Equipment of another type designed for direct measurement of density of mixtures conveyed in pipelines is a radioisotope instrument in which the effect of gamma ray absorption by the measured medium is used.

This type of instrument includes a gamma radiation source, said source being installed in the pipeline, and a system which receives the beam of radiation, said system translating the intensity of variations in absorption of rays by the mixture into an electric signal. This signal is then transmitted to an indicator-recording system. Operation of instruments of the above described type is based on principles other than measurement of electrical performance of the mixture and then on translating of variations in this performance into an electric or other signal.

One imperfection of instruments of the above described type is the complex construction required for the system translating the signal of the sensing element into an electric signal, while also there is a high time constant associated with inertia of the instruments, and a comparatively low accuracy of density measurements. Besides, in the case of using of a radioisotope-type instrument the operator may be exposed to harmful effects of radiation.

SUMMARY OF THE INVENTION

An object of the present invention is to develop an improved electric system for a meter of density of mixture conveyed in a pipeline, the characteristic qualities of the said system being a high accuracy of measurement, a minimum inertia of measurement, and a simple and safe operation.

This object is attained by an electromagnetic system of the density meter, said system comprising a capacity sensor installed in the pipeline and connected through a capacitance transducer with a system compensating temperature induced variations in capacity. Besides, there is a sensor installed in the pipeline, said sensor sensing the temperature and being connected either with the input of the system compensating the temperature induced variations in capacity, or with the capacitance transducer. The output of the said compensation system is connected with an indicator-recording system. In the case of the mixture temperature being constant or changing within a narrow range, the system includes a capacity sensor, said sensor being connected through the capacitance transducer directly with the indicator-recording system.

A creditable quality of the novel electric system for a density meter is the fact that the measurements of density of liquid conveyed in a pipeline are highly accurate and that their inertia is kept to a minimum. The improved system results is a meter which is safe and more convenient in operation.

BRIEF DESCRIPTION OF THE DRAWING

An embodiment of the invention will next be described by way of example and with reference to the accompanying drawing in which.

DESCRIPTION

Figure 1:
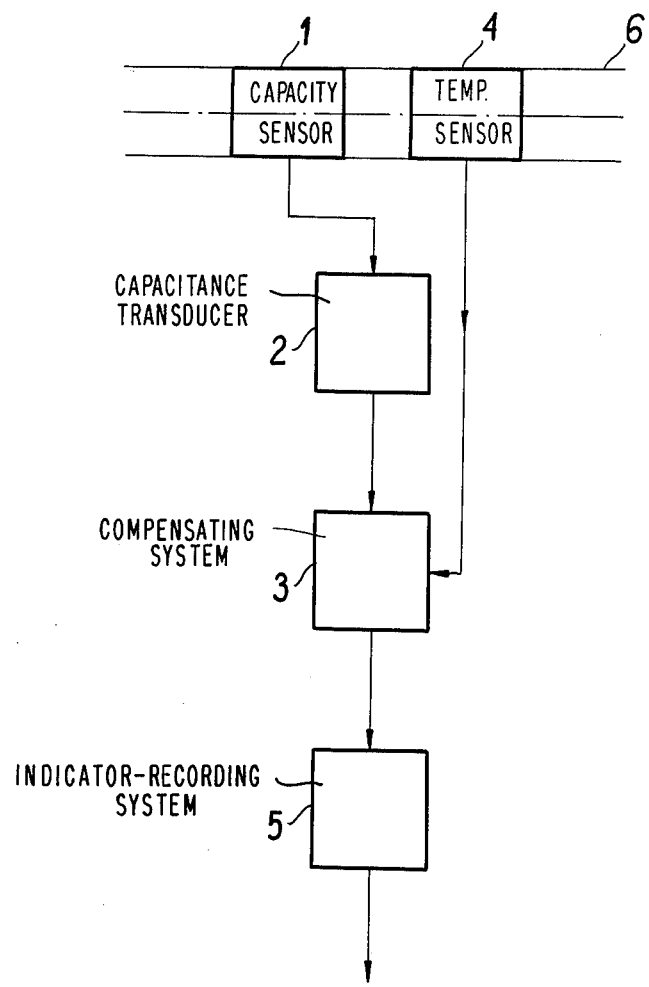
FIG. 1 illustrates the system in a comprehensive block diagram.
Figure 2:
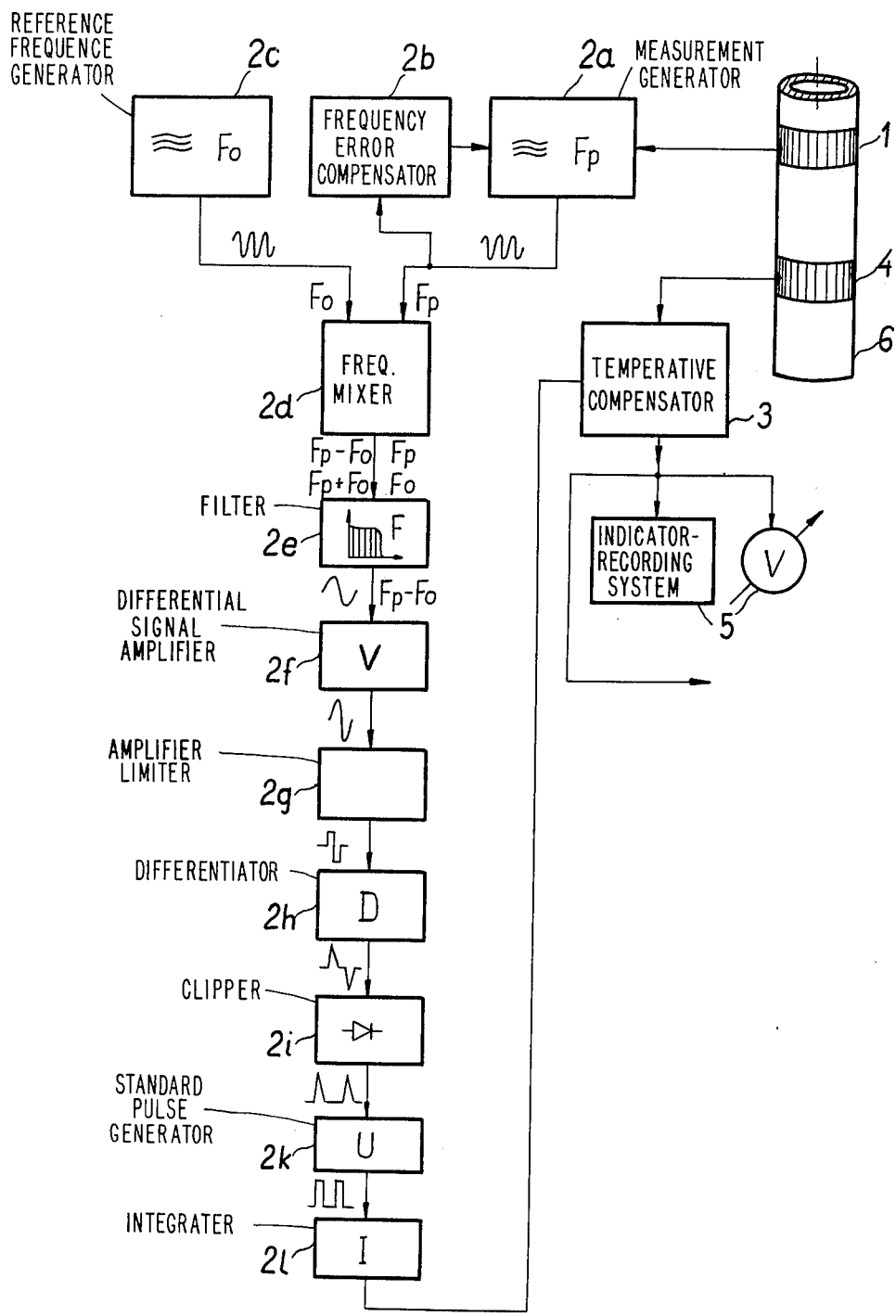
FIG. 2 illustrates the detailed construction of the system in a block diagram.

The system of the invention comprises a capacity sensor 1, the output of the said sensor being connected with a capacitance tranducer 2 (FIG. 1). The capacitance transducer 2 consists of a self-excited measurement generator 2a said generator being connected with a system 2b for compensating frequency error, and with a self-excited generator 2c suggesting a reference frequency.

Generators 2a and 2c are connected with a frequency mixer 2d. There is a low-pass filter 2e installed at the output of mixer 2d, said filter being connected, through a differential signal amplifier 2f and an amplitude limiter 2g, with a differentiating system 2h. There is a diode-type negative pulse clipper 2i provided at the output of the differentiating system 2h, said clipper being connected with a generator 2k of standard pulses, said generator being connected, in turn, with an integrating system 2l.

As has been already mentioned, the capacitance transducer 2 serves for conversion of capacity variations sensed by the capacity sensor 1 into a proportional voltage signal. The output of capacitance transducer 2 is connected with a system 3, said system compensating temperature induced variations in capacity, the input of the said system being connected with a temperature sensor 4 installed in a pipeline 6. The output of the system 3 compensating the temperature induced variations in capacity is connected with an indicator-recording system 5.

Instead of connecting it with the input of system 3, the temperature sensor 4 can be connected with the capacitance transducer 2, said transducer being connected directly with the indicator-recording system 5.

In the case of the temperature's being constant or changing within a narrow range, the system includes only the capacity sensor 1, said sensor being connected, through capacitance transducer 2, directly with the indicator-recording system 5.

The operation of the invented system is as follows. The capacitance variations sensed by the sensor 1, said variations being caused by variations in component content of a conveyed mixture, are used in re-modulating the frequency of the self-excited measurement generator 2a. The frequency variations of the said generator 2a, said variations being caused by variations in conductance of the conveyed liquid, are eliminated by means of compensation system 2b. the electric signals from generators 2a and from the thermic-coupled reference generator 2c are applied to the input of frequency mixer 2d, a measurement frequency Fp, a reference frequency Fo, and frequencies Fp – Fo being then obtained at the output of the said mixer. Only a differential frequency Fp – Fo is obtained at the output of the low-pass filter 2e, said frequency being amplified in the amplifier 2f. After a suitable treatment in the amplitude limiter 2g, in the differentiating system 2h, and in the negative pulse clipper 2i, this frequency releases generator 2k of standard pulses so, that the pulses of suitable repetition rate are obtained at the output of the said generator. The integrating system 2l counts these pulses and produces a signal which is proportional to the repetition rate. After a correction in the system 3 which compensates the temperature induced variations in capacity, this signal is applied to the indicator-recording system 5, said system being calibrated e.g. in the units of mixture density.

What we claim is:

1. An electric system for a meter for the measurement of the content of a mixture being conveyed in a pipeline, said system comprising a capacity sensor installed in said pipeline, a mixer, a compensation system for frequency variations, a capacitance transducer including a measurement generator having a first input connected to the capacity sensor, a second input connected to the compensation system for frequency variations and an output connected to said mixer, a reference frequency generator having an output connected to said mixer, a series circuit connected to the output of said mixer including a low-pass filter, an amplifier, an amplitude limiter, a differentiating system, a pulse clipper, a generator of standard pulses and an integrating system; the series circuit having an output, an indicator-recording means, means for compensating temperature coupling the output of the series circuit with the indicator-recording means, and a temperature sensor in said pipeline, said means for compensating temperature being connected with the temperature sensor.

2. A system as claimed in claim 1, wherein said compensation system for frequency variation includes means which eliminates variations of frequency of the measurement of generator caused by changes of loss tangent in the said mixture.

* * * * *